(12) United States Patent
Lutz et al.

(10) Patent No.: US 10,561,310 B2
(45) Date of Patent: Feb. 18, 2020

(54) LIGHTED BITE BLOCK

(71) Applicant: It's Lit Lighting Solutions LLC, Muskego, WI (US)

(72) Inventors: Thomas Lutz, Cedar Rapids, IA (US); Ernie Katris, New Berlin, WI (US); Phillip Bartoszek, New Berlin, WI (US); Peter Katris, Barrington, IL (US)

(73) Assignee: IT'S LIT LIGHTING SOLUTIONS LLC, Muskego, WI (US)

( * ) Notice: Subject to any disclaimer, the term of this patent is extended or adjusted under 35 U.S.C. 154(b) by 0 days.

(21) Appl. No.: 15/866,192

(22) Filed: Jan. 9, 2018

(65) Prior Publication Data

US 2018/0125349 A1    May 10, 2018

Related U.S. Application Data

(63) Continuation-in-part of application No. 14/725,960, filed on May 29, 2015, now abandoned.

(60) Provisional application No. 62/007,185, filed on Jun. 3, 2014.

(51) Int. Cl.
| | |
|---|---|
| *A61B 1/247* | (2006.01) |
| *A61C 1/08* | (2006.01) |
| *A61B 90/16* | (2016.01) |
| *A61B 1/06* | (2006.01) |
| *A61N 5/06* | (2006.01) |
| *A61B 1/32* | (2006.01) |

(52) U.S. Cl.
CPC ............ *A61B 1/247* (2013.01); *A61B 1/0684* (2013.01); *A61B 90/16* (2016.02); *A61C 1/088* (2013.01); *A61N 5/0613* (2013.01); *A61B 1/32* (2013.01)

(58) Field of Classification Search
CPC ......... A61B 1/24; A61B 1/0684; A61B 90/16; A61B 1/06; A61C 1/088; A61C 5/90
See application file for complete search history.

(56) References Cited

U.S. PATENT DOCUMENTS

| | | | | |
|---|---|---|---|---|
| 2,528,458 | A | * | 10/1950 | Stone ....................... A61B 1/24 600/212 |
| 4,167,814 | A | | 9/1979 | Schubert |
| 5,152,686 | A | * | 10/1992 | Duggan ............... A61C 17/043 433/140 |
| 6,022,214 | A | * | 2/2000 | Hirsch ..................... A61B 1/24 433/140 |
| 6,241,521 | B1 | | 6/2001 | Garrison |

(Continued)

FOREIGN PATENT DOCUMENTS

KR        100768030 B1 * 10/2007

OTHER PUBLICATIONS

Lexeon Emitter DS25 Technical Datasheet (Year: 2005).*

*Primary Examiner* — Christopher Stanford

(57) ABSTRACT

A bite block includes a body defining a first side wall, a second side wall, a first bite surface extending between the first side wall and the second side wall, and a second bite surface extending between the first side wall and the second side wall. A window is formed as part of the first side wall, an LED is positioned within the body and positioned to emit light through the window, and a power supply is positioned within the body and is connected to the LED. A switch is positioned within the body and is actuatable through the second side wall to selectively provide power to the LED.

21 Claims, 13 Drawing Sheets

(56) References Cited

U.S. PATENT DOCUMENTS

| | | | |
|---|---|---|---|
| 6,830,451 B1* | 12/2004 | Bayat | A61B 1/247 |
| | | | 433/140 |
| 8,905,924 B2 | 12/2014 | Khouri | |
| 9,095,297 B2* | 8/2015 | Khouri | A61C 5/90 |
| D782,048 S | 3/2017 | Ritter | |
| 9,585,551 B2 | 3/2017 | Cushner | |
| 2003/0134253 A1* | 7/2003 | Hirsch | A61C 17/04 |
| | | | 433/93 |
| 2005/0239018 A1* | 10/2005 | Green | A61C 5/90 |
| | | | 433/140 |
| 2008/0096155 A1* | 4/2008 | Khouri | A61C 1/088 |
| | | | 433/29 |
| 2008/0145813 A1 | 6/2008 | Crohn | |
| 2008/0166678 A1 | 7/2008 | Ramot | |
| 2009/0323370 A1 | 12/2009 | Koo | |
| 2012/0015320 A1 | 1/2012 | Koo | |
| 2012/0228528 A1 | 9/2012 | Koo | |
| 2013/0164702 A1* | 6/2013 | Khouri | A61B 1/24 |
| | | | 433/29 |
| 2013/0344454 A1 | 12/2013 | Nath | |
| 2014/0356802 A1 | 12/2014 | Balog | |
| 2015/0335394 A1 | 11/2015 | Khouri | |
| 2016/0310234 A1 | 10/2016 | Ritter | |

* cited by examiner

LIGHTED BITE BLOCK

CROSS-REFERENCE TO RELATED APPLICATIONS

This application is a continuation in part application of U.S. application Ser. No. 14/725,960 filed May 29, 2015, which claims priority to U.S. Provisional Application No. 62/007,185, filed Jun. 3, 2014, the entire contents of each are incorporated herein by reference.

FIELD OF THE INVENTION

The present invention relates to lighting systems for medical use, and in particular to lighting systems for the field of dentistry.

BACKGROUND OF THE INVENTION

Visibility during a dental procedure (e.g., within a patient's mouth) is a constant challenge for dentists, due to shadowing, tight spaces, and tools getting in the way during a dental procedure. Current lighting systems use high intensity lighting, overhead flood lights, head lamps, and mirrors to help provide lighting for the dentist during a procedure. However, these current systems are large, cumbersome, and expensive, and do not always provide the desired amount of light needed during a procedure.

SUMMARY

A bite block includes a body defining a first side wall, a second side wall, a first bite surface extending between the first side wall and the second side wall, and a second bite surface extending between the first side wall and the second side wall. A window is formed as part of the first side wall, an LED is positioned within the body and positioned to emit light through the window, and a power supply is positioned within the body and is connected to the LED. A switch is positioned within the body and is actuatable through the second side wall to selectively provide power to the LED.

Another bite block includes a first side wall defining a first surface arranged to be positioned between a patient's teeth and cheek, a second side wall defining a second surface arranged to be positioned between a patient's teeth and tongue, a first bite surface extending between the first side wall and the second side wall, and a second bite surface extending between the first side wall and the second side wall. The first bite surface is arranged at an oblique angle with respect to the second bite surface and each of the first bite surface and the second bite surface are positioned equidistant from a central axis. A first LED IS operable to emit white light and is positioned on the central axis and a second LED operable to emit light is positioned on the central axis and spaced apart from the first LED. A switch is operable to selectively provide power to one of the first LED, the second LED or both the first LED and the second LED.

Other aspects of the invention will become apparent by consideration of the detailed description and accompanying drawings.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limited.

DETAILED DESCRIPTION

Figure 1:
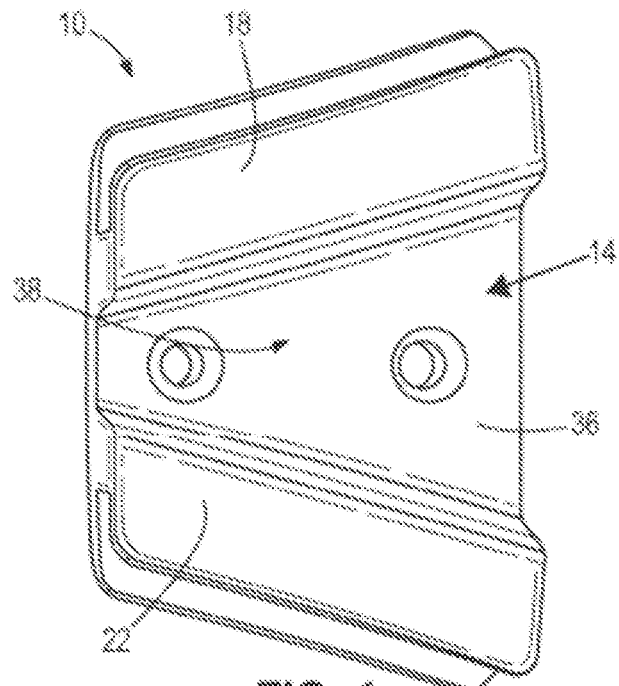
FIG. 1 is a top view of a dental bite block.
Figure 2:
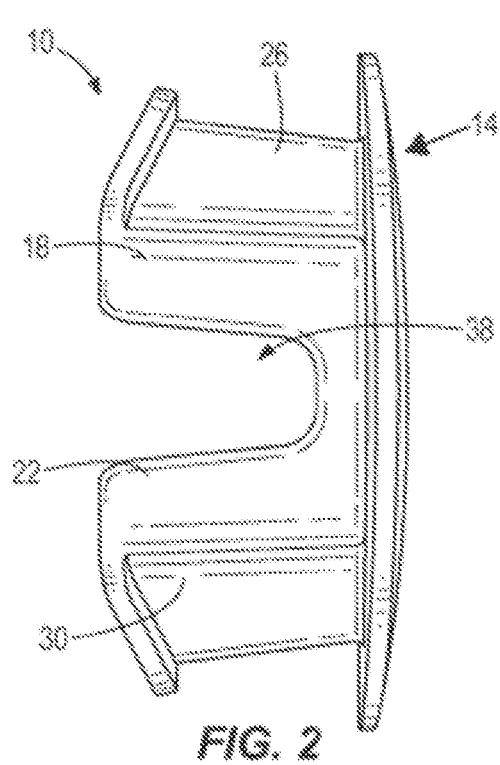
FIG. 2 is a left side view of the bite block of FIG. 1.
Figure 3:
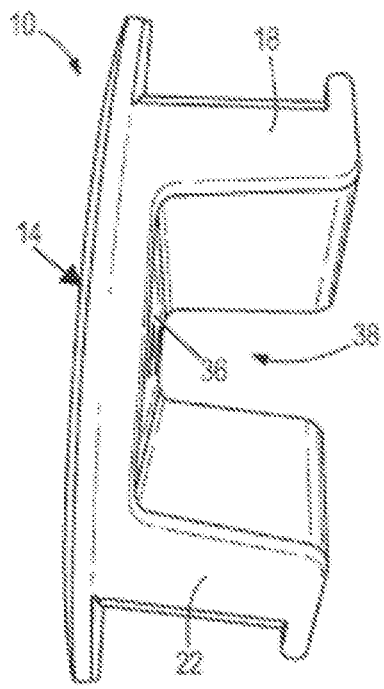
FIG. 3 is a right-side view of the bite block of FIG. 1.

FIGS. 1-3 illustrate a dental bite block 10. The illustrated bite block 10 is a resilient, wedge-shaped structure that includes a main body portion 14, a first bite element 18 that extends from the main body portion 14, and a second bite element 22 that extends from the main body portion 14. In the illustrated construction the main body portion 14, the first bite element 18, and the second bite element 22 are integrally formed as one piece. The first and second bite elements 18, 22 are angled relative to one another at an acute angle, and include biting surfaces 26 and 30, respectively (FIG. 2). In use, the patient bites down on the biting surfaces 26, 30 to press the first and second bite elements 18, 22 toward one another. The bite elements 18, 22 provide resistance, and maintain the patient's mouth in an open position, thereby providing access for dental tools.

The illustrated bite block 10 is re-usable through sterilization in an autoclave or other suitable process. However, in some constructions the bite block 10 is disposable, and is intended only for a one-time use.

Figure 4:
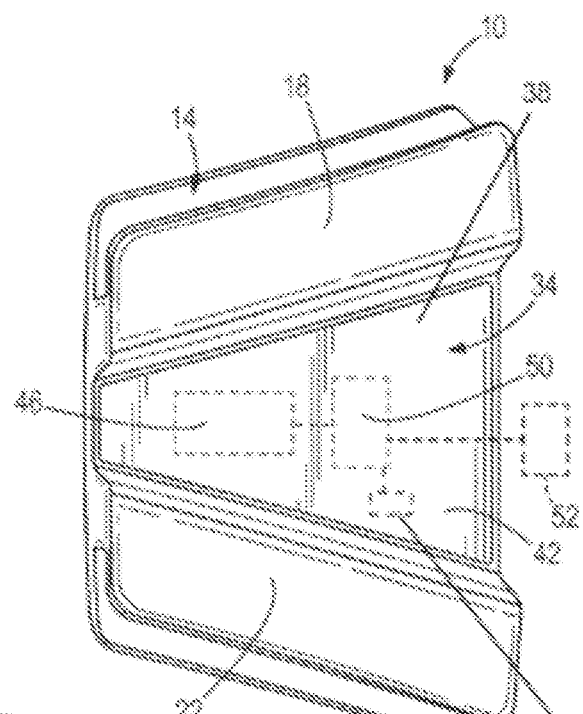
FIG. 4 is a top view of the bite block of FIG. 1, with a lighting element coupled to the bite block.

With reference to FIGS. 1-5, in some constructions the bite block 10 includes a lighting element 34 (FIGS. 4 and 5) disposed on an interior surface 36 (FIGS. 1-3) of the body portion 14 within a channel 38, the channel 38 being formed by the interior surface 36, the first bite element 18, and the second bite element 22. As illustrated in FIG. 4, the lighting element 34 includes a housing 42 (e.g., a thin housing), a battery 46 disposed within the housing, and a light-emitting element 50 (e.g., a light-emitting diode ("LED")) disposed within the housing 42 that is powered by the battery 46. The battery 46 and light-emitting element 50 are illustrated schematically. In some constructions, the battery 46 is a single, thin, button cell battery such as that used in watches (e.g., a 1-3 Volt type battery). Other constructions include different numbers and types of batteries, as well as different numbers of light-emitting elements 50. In the illustrated construction, the housing 42 is a waterproof compartment. In some constructions, a portion of the light-emitting element 50 is disposed outside of the housing 42.

The illustrated lighting element 34 is removable from the bite block 10. For example, in some constructions the lighting element 34 fits into the channel 38 via only a frictional hold. However, in some constructions the lighting element 34 is integrally formed as one inseparable piece with the bite block 10 (e.g., with one or more of the main body portion 14, the first bite element 18, and the second bite element 22).

In some constructions, the lighting element 34 is disposed along or within other areas of the bite block 10 than within the channel 38. For example, in some constructions the lighting element 34 is formed into an area of the main body portion 14 itself.

The lighting element 34 emits light from the light-emitting element 50 and illuminates the inside of a patient's mouth. The lighting element 34 provides significant amounts of light in regions within the mouth where it is otherwise difficult to generate light. In some constructions, the lighting element 34 also illuminates an area outside of and surrounding the patient's mouth.

The illustrated lighting element 34 provides non-specific flood lighting within the patient's mouth. In some constructions, the bite block 10 is made of transparent material to create more of an overall glow and flooding of light within the mouth. In other constructions, the lighting element 34 provides more specific, directed lighting (e.g., lighting that is focused or aimed towards a particular area within a patient's mouth, such as a tooth or teeth).

In some constructions, the wavelength of the light emitted from the lighting element 34 is designed specifically for a particular dental procedure. For example, in some constructions a specific wavelength (e.g., a wavelength corresponding to blue or ultraviolet light) is used to help identify and observe cavities within a patient's mouth or to better illuminate a die or stain.

In the illustrated construction, the light-emitting element 50 is turned on by a remote switch 52 (e.g., a magnetic switch, illustrated schematically in FIG. 4). In other constructions, the light-emitting element 50 is turned on by a physical switch on the lighting element 34 itself. In some constructions, the battery 46 is rechargeable. For example, in some constructions the battery 46 is recharged wirelessly via an inductive recharge.

While the lighting element 34 is illustrated in the context of a wedge-shaped bite block 10, in other constructions the lighting element 34 is used with (e.g., is integrally formed as one piece with, or releasably coupled to) other types of common bite blocks commonly used in the field of dentistry.

In use, a dentist or hygienist places the bite block 10, with the lighting element 34 coupled thereto, into a patient's mouth. The lighting element 34 is turned off when it is initially placed into the patient's mouth. However, in some constructions the lighting element 34 is already turned on. Once the bite block 10 is inserted into the mouth, the patient bites down on the bite elements 18, 22. The compression of the bite elements 18, 22 causes some stress on the housing 42 of the lighting element 34. However, the housing 42 is able to withstand this limited stress. Once the bite elements 18, 22 are engaged the lighting element 34 is turned on (e.g., with the switch 52). In some constructions, the act of biting on the bite block 10 actuates the lighting element 34. The lighting element 34 illuminates at least a portion of the interior of the patient's mouth. The dentist may then conduct a procedure in the mouth with sufficient lighting. Once the procedure is finished, the lighting element 34 is turned off, and the bite block 10 and lighting element 34 are removed (e.g., to be discarded or autoclaved).

Figure 5:
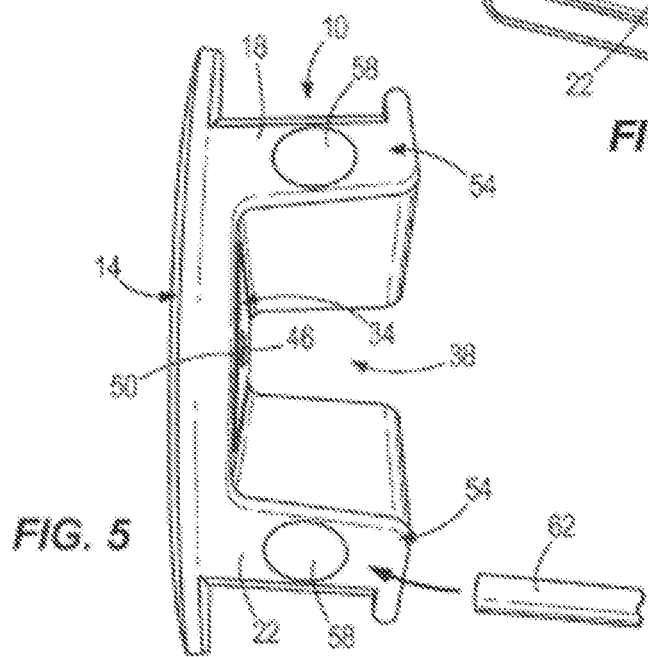
FIG. 5 is a right-side view of the bite block of FIG. 1, with a saliva channel for attachment to a suction tool.

With reference to FIG. 5, in some constructions the bite block 10 additionally or alternatively includes one or more saliva channels 54. As illustrated in FIG. 5, the channels 54 are formed into the first and second bite elements 18, 22. The channels 54 include a connection 58 for a suction tool 62 (e.g., hose) or adaptor to connect to the suction tool 62. The channels 54 facilitate hands-free removal of saliva during a dental procedure. Other constructions include different numbers and locations for the channels 54.

Figure 6:
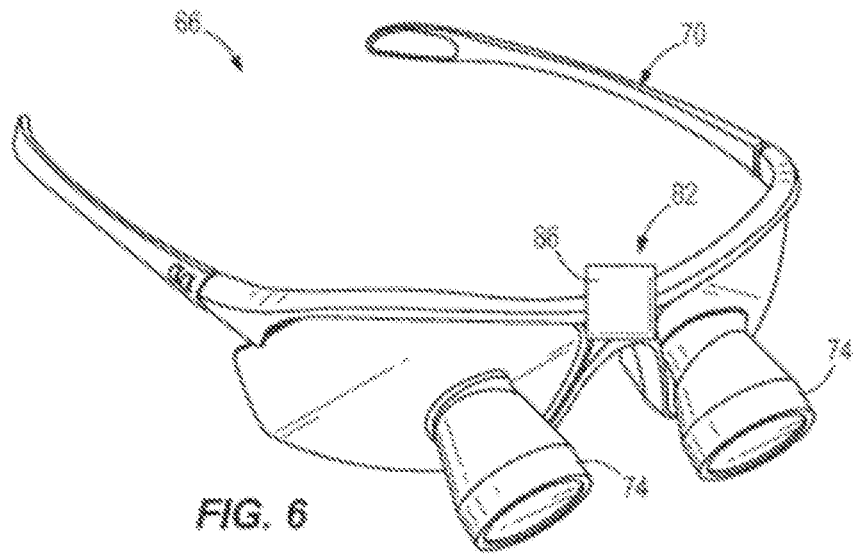
FIG. 6 is a perspective view of a pair of surgical glasses, with loupes and a bracket for attachment of a lighting element.
Figure 7:
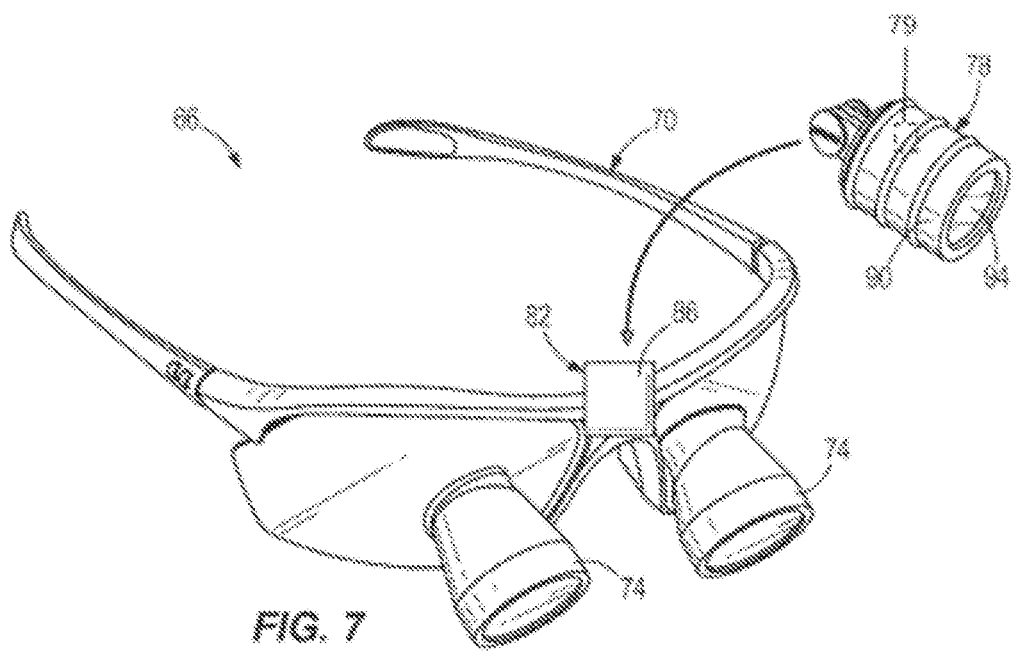
FIG. 7 is a perspective view of the pair of surgical glasses of FIG. 6, illustrating the lighting element being attached to the bracket.
Figure 8:
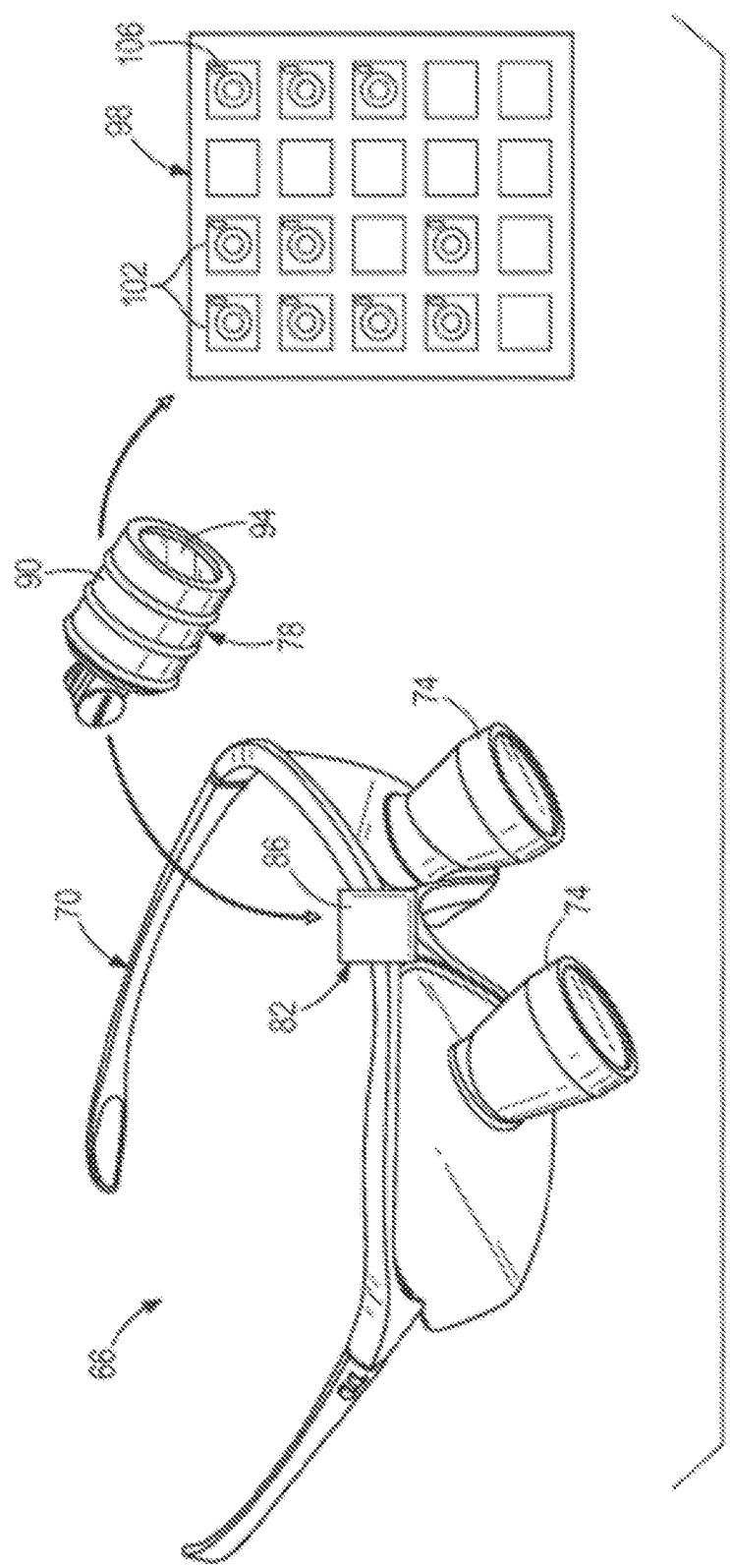
FIG. 8 is a perspective view of a lighting system that includes the pair of surgical glasses of FIG. 6, as well as a charging station for charging additional lighting elements.

FIGS. 6-8 illustrate a head element 66 that is worn by a dentist during a procedure (e.g., during a procedure in which the bite block 10 and the lighting element 34 are also used). The head element 66 includes a pair of surgical glasses 70 worn over the dentist's ears and nose, two loupes 74 that are coupled to the glasses in front of the dentist's eyes, a removable lighting element 78 (FIGS. 7 and 8) disposed above the dentist's nose, and a mounting bracket 82 (illustrated schematically) that releasably couples the lighting element 78 to the glasses 70.

The illustrated mounting bracket 82 is a quick-connect element (e.g., allowing the lighting element 78 to snap in and out with ease), and is adjustable to fix the lighting element 78 into one or more pre-determined and reproducible positions based on the dentist's preference. For example, in some constructions the mounting bracket 82 includes an adjustment mechanism 86 (e.g., a tactile, snap, or ratchet-type mechanism) that provides an indication of the angle of the lighting element 78 relative to the glasses 70 and/or the loupes 74.

As illustrated in FIGS. 7 and 8, the lighting element 78 includes a housing 90 that houses a battery (e.g., lithium-ion, not shown) and one or more light-emitting elements 94 (e.g., an LED). The battery is configured to last approximately 2-4 hours before it needs to be recharged. This allows for a smaller battery and housing 90, and minimizes the overall weight of the lighting element 78. Other constructions include different ranges of battery life.

With reference to FIG. 8, once the battery power is exhausted in the lighting element 78, the lighting element 78 is removed and swapped with a new, identical, fully-charged lighting element 78 from a remote charging assembly 98. The new lighting element 78 is quickly and easily coupled to the mounting bracket 82, already in the user's preferred position or angle due to the adjustment mechanism 86.

The used lighting element 78 is then charged on the charging assembly 98. The illustrated charging assembly 98 is a multi-station charger having a plurality of stations 102 to receive and hold lighting elements 78. In some constructions, the charging assembly 98 is a single-station charger. As illustrated in FIG. 8, each of the stations 102 includes an indicator light 106 that illuminates or changes color when lighting element 78 is disposed within the charging assembly 98 and/or indicates a state of the charge.

The lighting elements 78 are modular, cost-effective, light-weight, and efficient. While a battery life, for example, of 2-4 hours is significantly less than a full day of battery life, the use of the charging assembly 98 and the ease of coupling and de-coupling the lighting elements 78 to the glasses 70 makes the lighting elements 78 ideal for a variety of medical procedures and operating environments.

Figure 9:
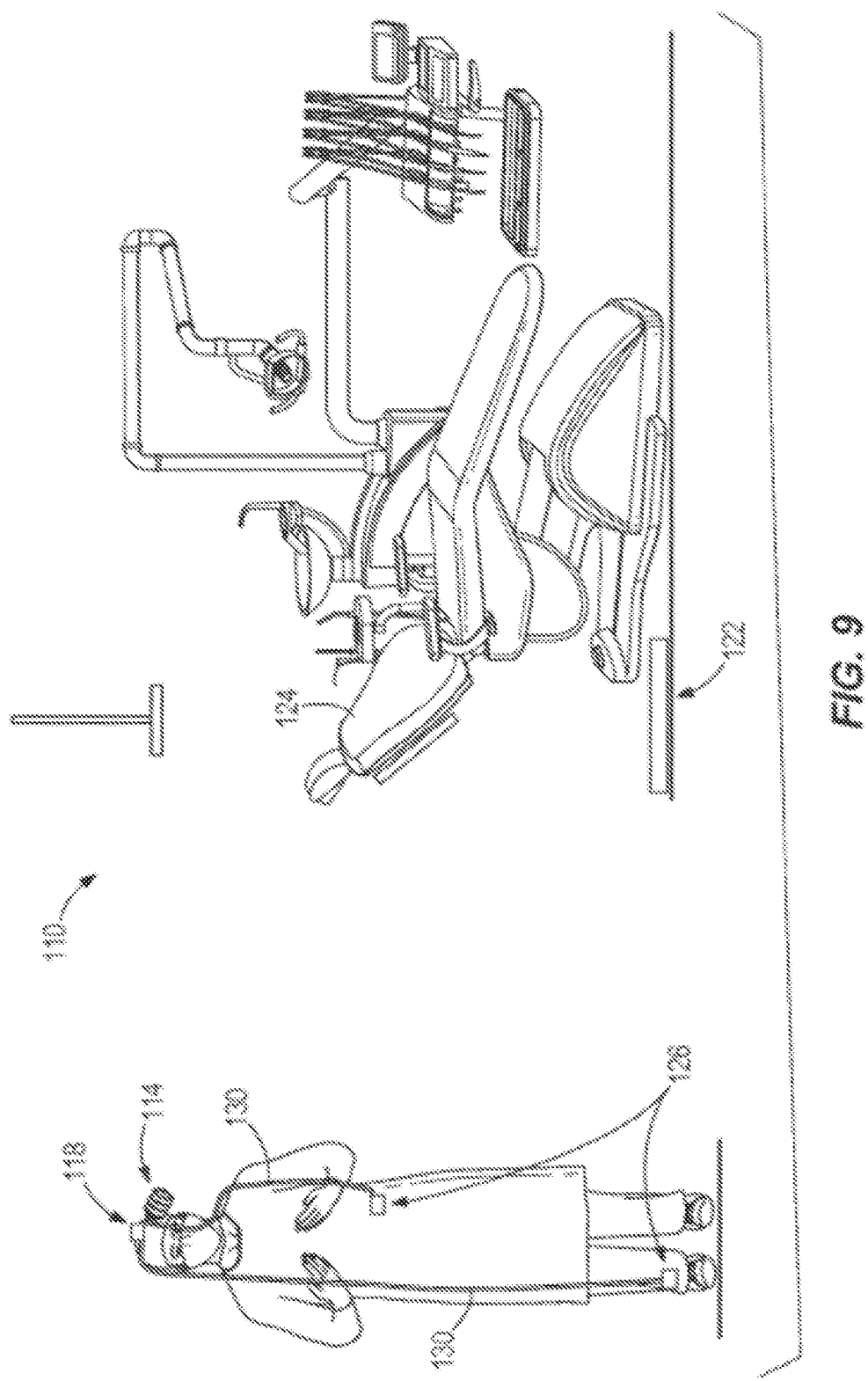
FIG. 9 is a front view of an induction system for use in a medical environment, with a lighting element that is not energized.
Figure 10:
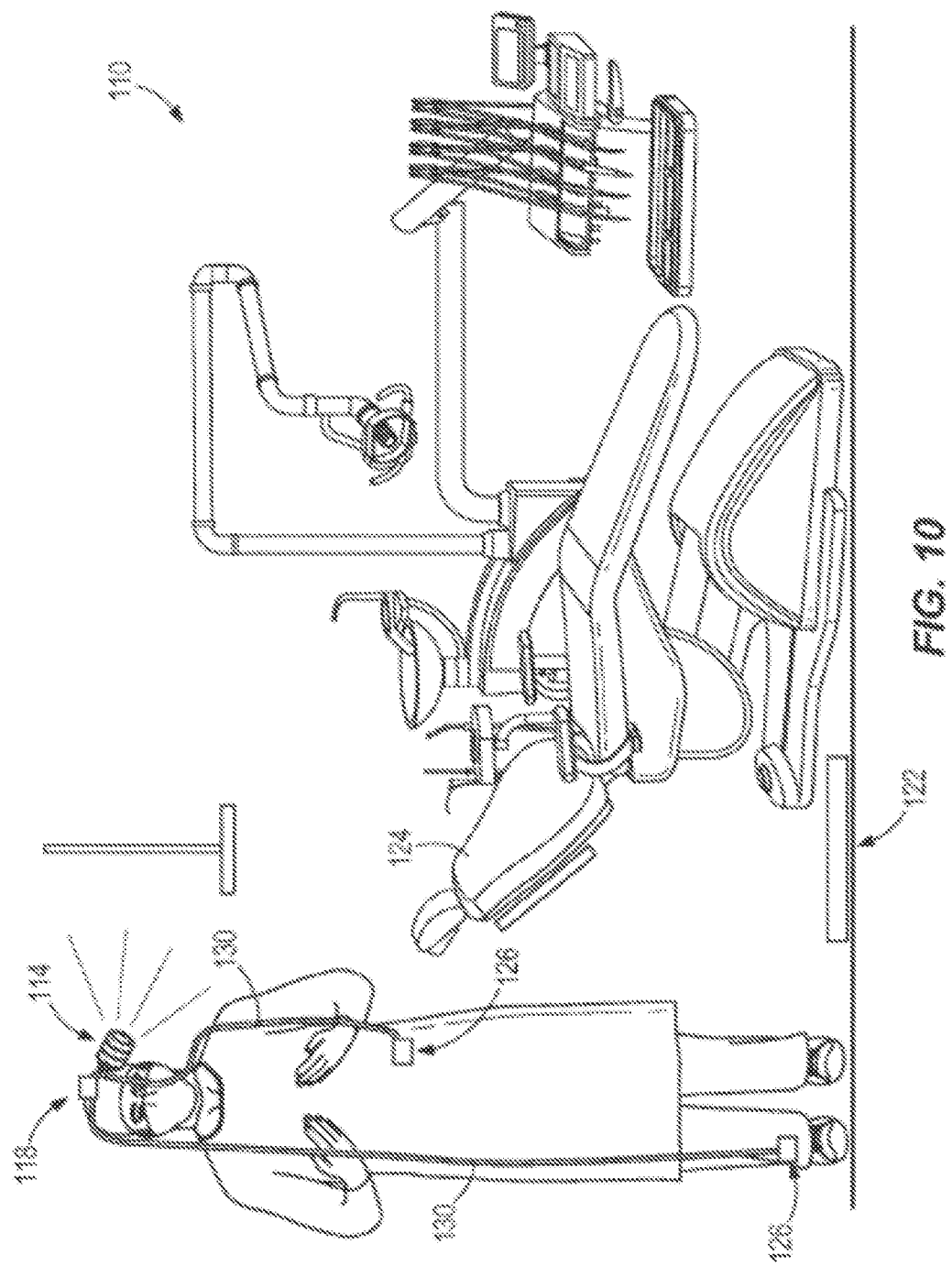
FIG. 10 is a front view of the induction system of FIG. 9, wherein the lighting element is energized.

With reference to FIGS. 9 and 10, in some constructions inductive power is used to turn on one or more lighting elements or other tools. For example, FIGS. 9 and 10 illustrate an induction system 110 for use in a medical environment that includes a lighting element 114 turned off (FIG. 9) and turned on (FIG. 10) by induction. The illustrated lighting element 114 is a headlamp (e.g., with an LED) worn by a dentist. However, other constructions include different types of lighting elements. In some constructions, the induction system 110 is used to turn on the lighting element 34 of the bite block 10 and/or the lighting element 78 described above (e.g., by replacing the batteries). In some constructions, the induction system 110 is used to turn on medical tools other than lighting elements (e.g., brushes, drills, etc.). As noted above, in some constructions the battery 46 for the lighting element 34 of the bite block 10 is recharged wirelessly via an inductive recharge, which may be supplied for example by the power induction plate 122 of the induction system 110.

With reference to FIGS. 9 and 10, the illustrated induction system 110 includes an induction coil 118 that is worn on the dentist's head (e.g., on a strap, cap, or other head-piece). The induction coil 118 is located adjacent to the lighting element 114 and is connected with direct wiring to the lighting element 114. In some constructions, the induction coil 118 and the lighting element 114 are integrally formed together as one unit or structure. In some constructions, the lighting element 34 of the bite block 10 is turned on or recharged by the induction system 110, and the lighting element 34 includes an induction coil 35 (FIG. 4). In some constructions, the lighting element 78 is turned on or recharged by the induction system 110, and the lighting element 78 includes an induction coil 79 (FIG. 7).

With continued reference to FIGS. 9 and 10, the lighting system 110 also includes at least one power induction plate 122 that generates an inductive field to power (e.g., turn on, charge, recharge, etc.) one or more tools. In the illustrated construction, the power induction plate or plates 122 are located within a medical environment (e.g., under each table/chair, within a floor mat, in the ceiling, etc.). As illustrated in FIG. 9, in some constructions the power induction plate 122 is adjacent a dentist chair 124. When an induction coil 118 is located within a predefined area surrounding the power induction plate 122 (e.g., within a radius of two feet, five feet, ten feet, etc.), a current is generated within the induction coil 118 that powers the lighting element 114 (e.g., turns the lighting element 114 on).

With continued reference to FIGS. 9 and 10, in some constructions one or more remote induction coils 126 (e.g., in receiver packs) are instead or additionally located on the dentist's waist, belt, near the dentist's ankles, shoes, etc. These induction coils 126 are coupled to the lighting element 114 via wires 130. Similar to the induction coil 118, when the remote induction coil or coils 126 are located close to the power induction plate 122 (e.g., within two feet, five feet, ten feet, etc.), a current is generated within the induction coil or coils 126 that powers the lighting element 114.

In some constructions, the use of induction power in the induction system 110 eliminates the need for power cords and battery packs. The use of induction power (including the arrangement of the power induction plates 122 and induction coils 118, 126) also minimizes overall power requirements for an operating setting while maximizing transmission efficiencies.

In some constructions, the lighting element 114 includes an on/off switch. In some constructions, the "on" position automatically turns "off" when the dentist leaves the inductive field generated by a power induction plate 122, and/or vice versa. Thus, when the dentist moves from one chair to another continuously throughout a day he or she would not have to turn the lighting element 114 on and off. Rather, when the dentist sits in a chair and approaches a patient the lighting element 114 automatically becomes energized by the power induction plate 122 beneath the chair and subsequently de-energized upon retreating from the patient. In some constructions, there is an on/off foot switch or other switch that allows the power induction plate 122 to be turned on and off "hand's free" which likewise provides operation without power cords and battery packs.

While FIGS. 9 and 10 illustrate a dental operating environment, the induction system 110 is also applicable to other operating environments. In particular, the induction system 110 provides benefit for operating environments that are awkward to access, require fine dexterity skills of the professional, and benefit from reduced numbers of cords, equipment, switches, and other objects or materials that may interfere with medical personnel or patients during a procedure. Induction-powered devices are further able to reduce procedure time by alleviating issues such as large battery size, the need to recharge a battery, and reduced battery power that often occurs toward the end of a battery's life.

Figure 11:
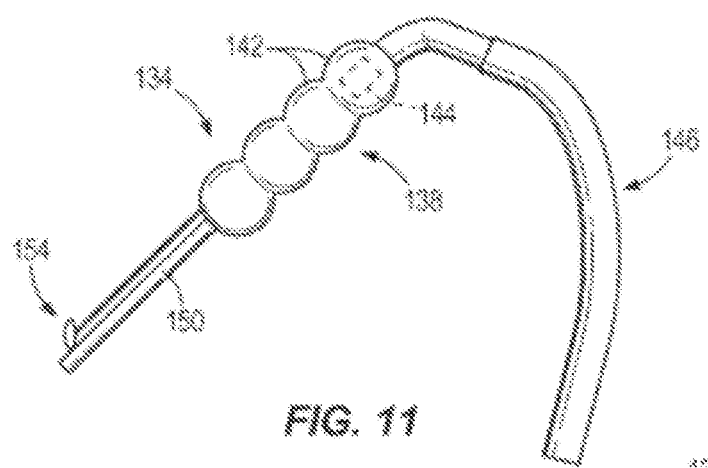
FIG. 11 is a perspective view of a medical tool that includes a lighting element and a heated handle.
Figure 12:
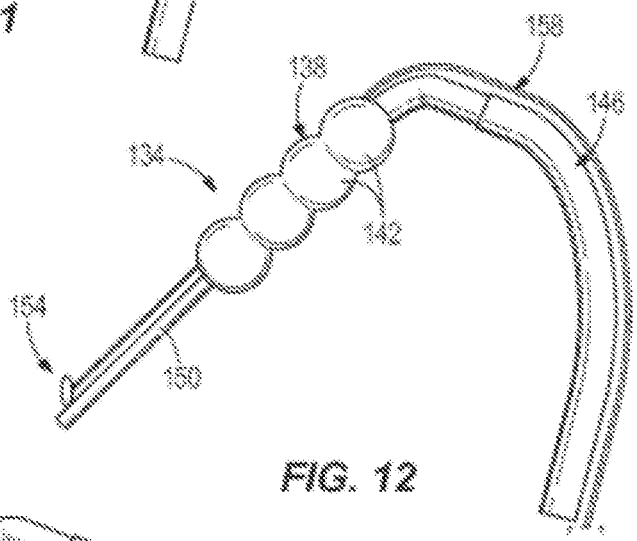
FIG. 12 is a perspective view of the medical tool of FIG. 11 being powered by a separate power cord.
Figure 13:
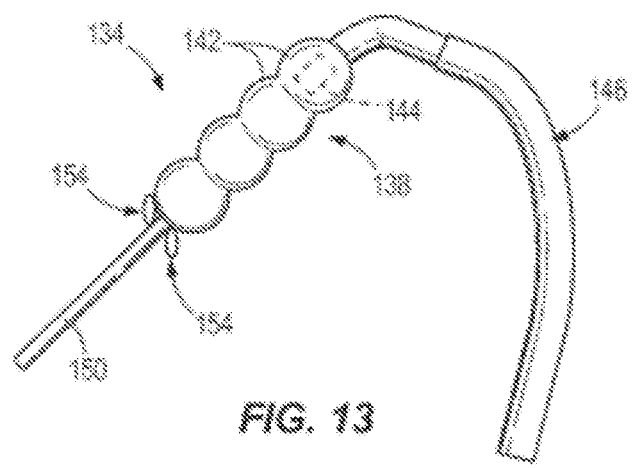
FIG. 13 is a perspective view of the medical tool of FIG. 11, wherein the medical tool includes multiple lighting elements disposed adjacent the handle.

FIGS. 11-13 illustrate a medical tool 134 that is both heated and lighted. The illustrated tool 134 is a suction tool for use in a dental procedure. However, in other constructions the tool 134 is any other medical tool that benefits from both heating and lighting.

With reference to FIG. 11, the tool 134 includes a handle 138 having a plurality of ridges 142 that facilitate gripping of the tool 134. The handle 138 is heated via a power source 144 (e.g., a battery disposed within the handle 134, illustrated schematically in FIGS. 11 and 13). The ridges 142 provide an ergonomic gripping surface, such that the user's hand does not cramp or otherwise become uncomfortable after gripping the tool 134 for an extended period of time (e.g., 30 or more minutes). The heating provided in the handle 138 further alleviates discomfort, and along with the ergonomic gripping surface, inhibits the development of carpal tunnel syndrome.

The tool 134 further includes a suction line 146 that is coupled to the handle 138 and passes through or alongside the handle 138. The suction line 146 is coupled to a vacuum source (not shown) to generate a sucking action at a distal end 150 of the suction line 146. A lighting element 154 (e.g., an LED) is coupled to the distal end 150. The lighting element 154 provides illumination in a patient's mouth when the distal end 150 is placed in the patient's mouth, similar to the lighting element 34 described above. The lighting element 154 is powered by the same power source 144 (e.g., battery) as the handle 138. In other constructions, the handle 138 and the lighting element 150 have separate power sources. In some constructions, the tool 134 is powered by the induction system 110. For example, in some constructions the handle 134 (or other element on the tool 134) includes an induction coil as the power source 144 or as part of the power source 144, and the power source for the handle and/or lighting element 154 is an induction field generated by a power induction plate (e.g., one of the power induction plates 122 described above).

With reference to FIG. 12, in some constructions one or more of the handle 138 and the lighting element 154 are heated and powered via a wired connection 158 to a remote power source 144. With reference to FIG. 13, in some constructions one or more lighting elements 154 are disposed adjacent the handle 134 to provide maximum flood-type illumination from the tool 130.

In the illustrated construction, the handle 138 is removable, and is cleaned and sterilized (e.g., via autoclave) after each use before being re-attached to the suction line 146. In the illustrated construction, the lighting element or elements 154 are also removable, and are cleaned and sterilized (e.g., via autoclave) after each use before being re-attached to the suction line 146. In some constructions, the suction line 146 is disposable after a single use, such that a new suction line 146 is used with each use of the tool 134.

FIGS. 14-18 illustrate another construction of a bite block 200. The bite block includes a body 204 that defines an interior 208 in which a power supply 212, at least one LED 214, and a switch 218 are located.

The illustrated bite block 200 includes a first side wall 222 and a second side wall 224 spaced apart from the first side wall 222. In the illustrated construction, the first side wall 222 and the second side wall 224 are substantially planar. However, other constructions may include walls 222, 224 that are curved to better fit a patient's mouth. A first bite surface 228 and a second bite surface 232 extend between the first side wall 222 and the second side wall 224 and are sized to generally fit over a patient's teeth. The first bite surface 228 and the second bite surface 232 are arranged at an oblique angle with respect to one another (e.g., 30 degrees) to accommodate positioning between the upper and lower teeth of a patient with the mouth in the open position. Each of the first bite surface 228 and the second bite surface 232 are equidistant from an axis 236 or plane that extends between the front and rear of the bite block. In addition, a plurality of ribs 240 extends from each bite surface 228, 232 with each rib 240 having a triangular cross section. The ribs 240 provide a non-slip positioning surface for the patient's teeth and reduce fatigue. Of course, other shapes for the ribs 240 are possible.

End walls 244 extend between the first side wall 222, the second side wall 224, the first bite surface 228, and the second bite surface 232 to complete the body 204 of the bite block 200 and to enclose the space 208. In preferred constructions, the body 204 is an inseparable component that cannot be disassembled without destroying the body 204. This arrangement assures that the space 208 is water-tight and also assures that the body 204 is a single use product, as sterilizing the bite block 200 would be impractical and would damage the components disposed within the space 208. In addition, because the bite block 200 is intended to be a single use device, materials can be selected without considering their ability to be sterilized. The body 204 is preferably made using a resilient material (e.g., Shore A 60-70). In one construction, the body 204 is over-molded with a thermoplastic elastomer (TPE) having the desired resiliency. In addition, in preferred constructions, the body 204 of the bite block 200 is substantially opaque to control the distribution of light within the patent's mouth. However, some constructions could employ a translucent body 204 or a body 204 that includes translucent portions.

Figure 14:
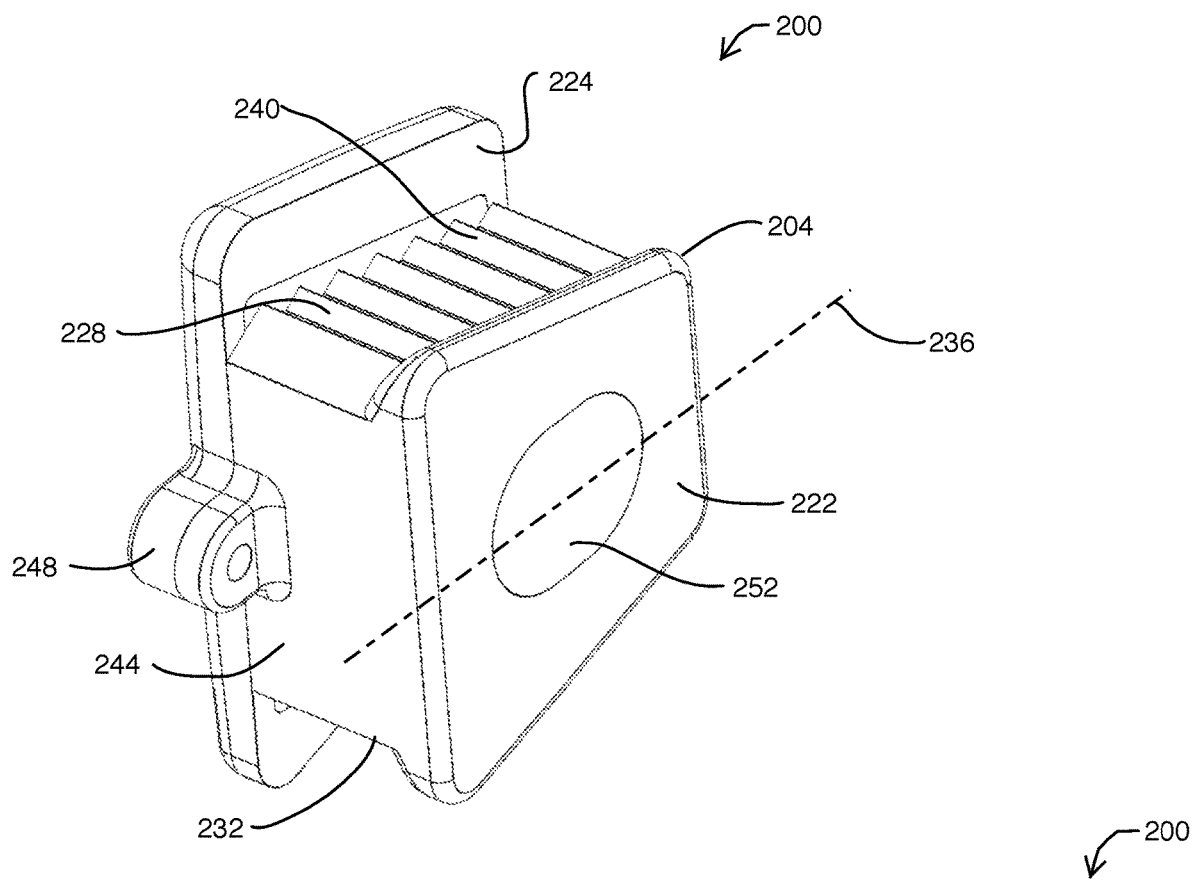
FIG. 14 is perspective view of a bite block including lights.
Figure 15:
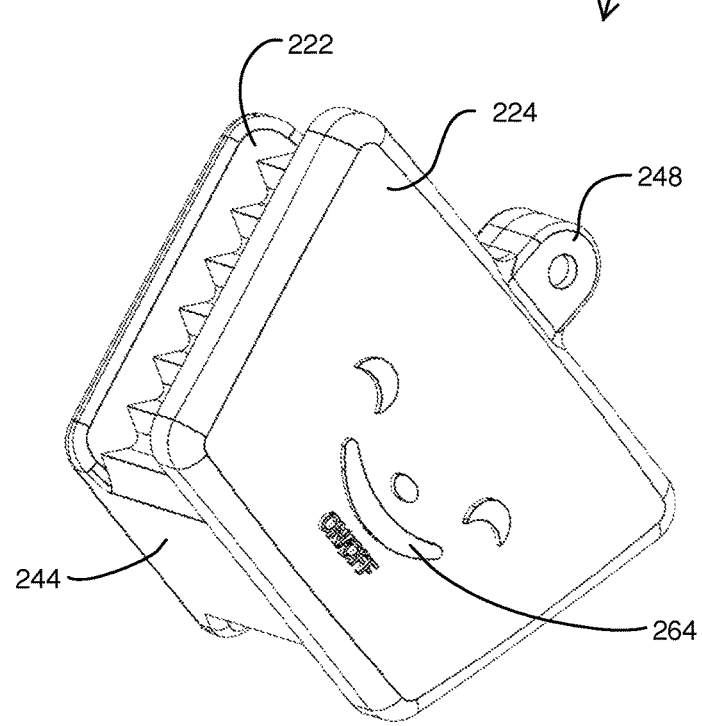
FIG. 15 is another perspective view of the bite block of FIG. 14.

With continued reference to FIGS. 14 and 15, the bite block 200 also includes a floss retractor 248 that extends from one end of the bite block 200 (the end positioned on the lip side of the mouth when in use) and includes an aperture for receiving dental floss or any other suitable material. The dental floss, or other material, can be used to easily retract the bite block 200 from a patient should such an extraction be required.

Figure 22:
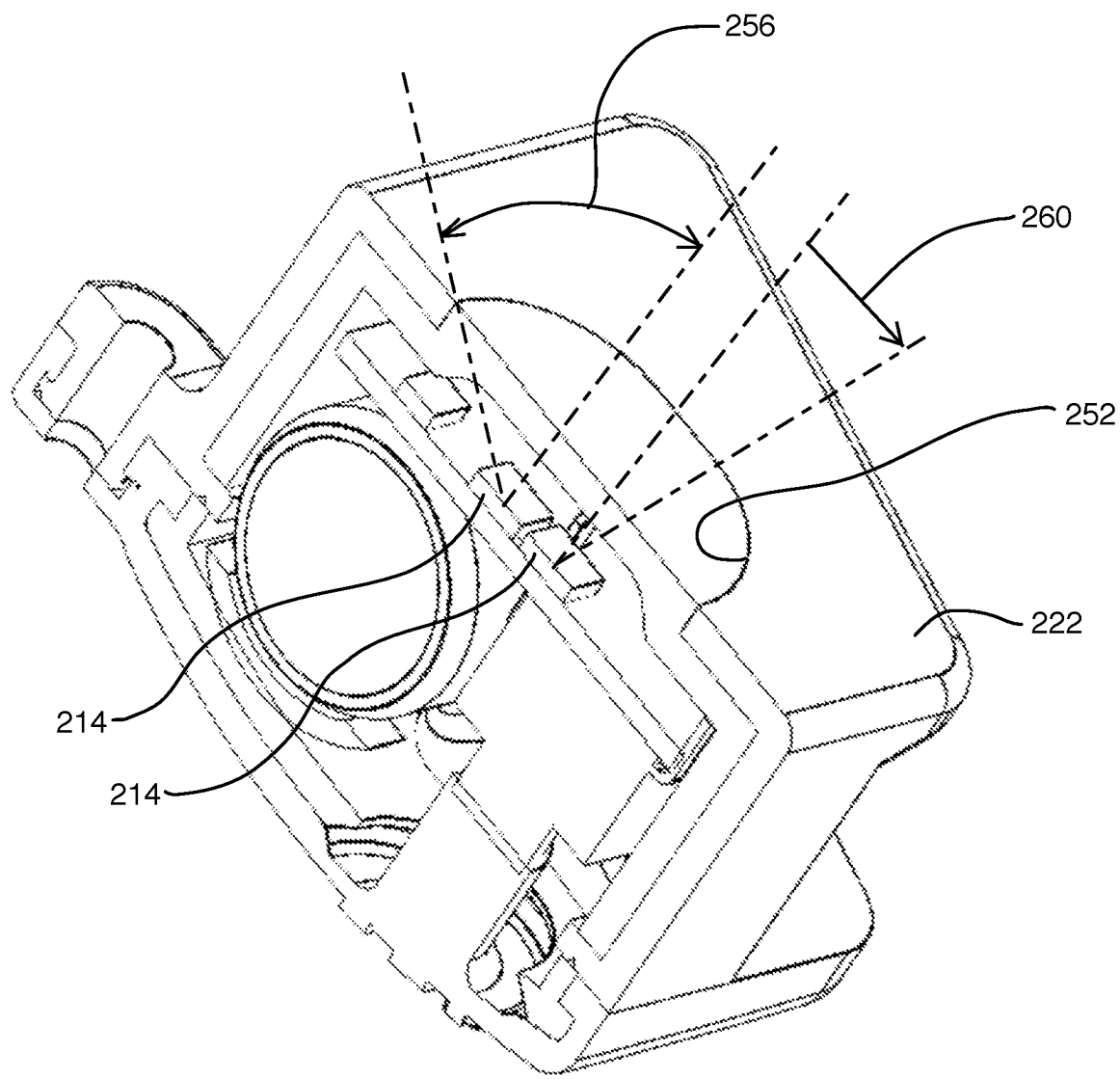
FIG. 22 is a perspective section view illustrating the arrangement of the LEDs.

As illustrated in FIG. 14, the first side wall 222 includes a window 252 that faces into the patient's mouth when the bite block 200 is properly positioned. The window 252 is fixedly attached to the first side wall 222 such that a water tight seal is formed therebetween. The window 252 is preferably transparent to allow light from the LEDs 214 to easily pass through. In some constructions, the window 252 is shaped to provide a lens that focuses the light, directs the light, or otherwise affects the light that passes through the window 252. In the illustrated construction, the window 252 is sized, shaped, and positioned to optimize the emission of light from two LEDs 214 having a dispersion angle 256 of 120 degrees as shown in FIG. 22. If LEDs 214 with different dispersion angles 256 are used, a different size and shape may be required for the window 252. Additionally, if the LEDs 214 are aligned differently the window 252 could also be modified. FIG. 22 illustrates two LEDs 214 with one LED illustrating the dispersion angle 256 and the other illustrating an LED 214 that is tipped at an angle 260 toward the rear of the patient's mouth. The window 252 could also include a movable element (e.g., rotatable, translatable, etc.) that allows the user to change the focus or direction of the light.

With reference to FIG. 15, a switch actuator 264 is formed as part of the second side wall 224. The switch actuator 264 provides for actuation of the switch 218 to transition the LED 214 between their various modes of operation (e.g., on, off, etc.). The positioning of the switch actuator 264 enhances the operation of the bite block 200 by reducing the likelihood of false actuations during the dental procedure. For example, if the switch actuator 264 were positioned on the tongue side of the bite block 200 adjacent the window 252, it would be more likely that dental tools or the patient's tongue would inadvertently contact the switch actuator 264 during a procedure. Additionally, the placement of the switch actuator 264 on the cheek side of the patient allows for easy access by the users to switch the LEDs 214 between modes by using a finger inside of the cheek. In other constructions, the switch actuator 264 can be actuated by touching the exterior of the patient's cheek. In still other constructions, the switch 218 is actuated using a magnetic device, or key positioned adjacent the switch actuator 264 outside of the patient's mouth.

Figure 16:
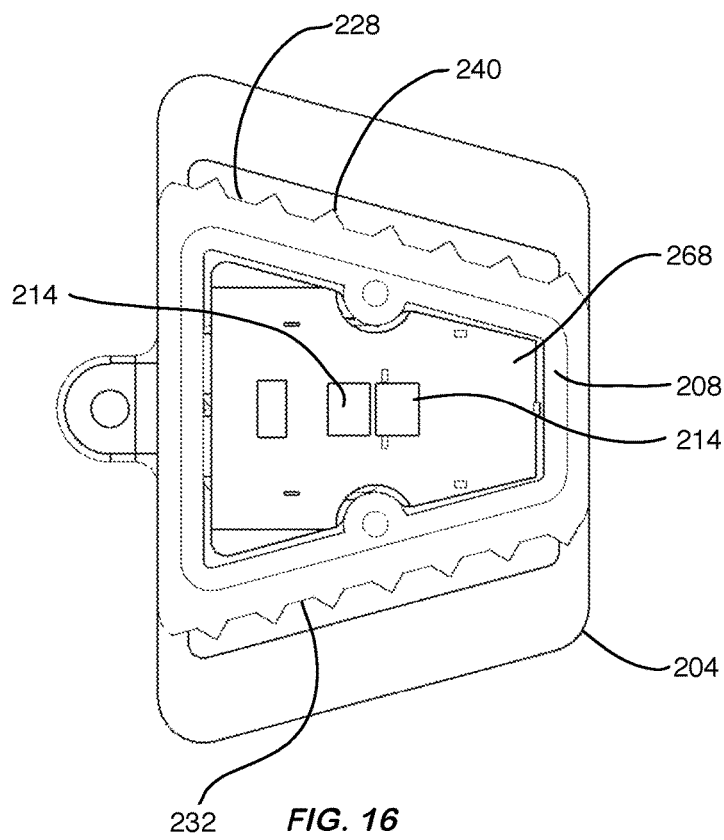
FIG. 16 is side view of the bite block of FIG. 14 with a side surface removed to illustrate the components within the bite block.
Figure 17:
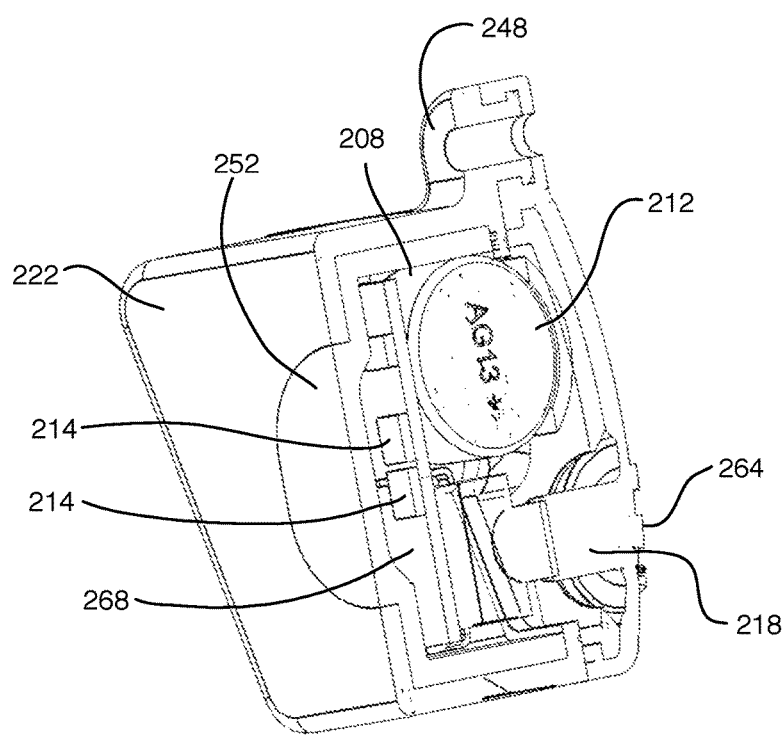
FIG. 17 is perspective section view of the bite block of FIG. 14 illustrating the components within the bite block.
Figure 18:
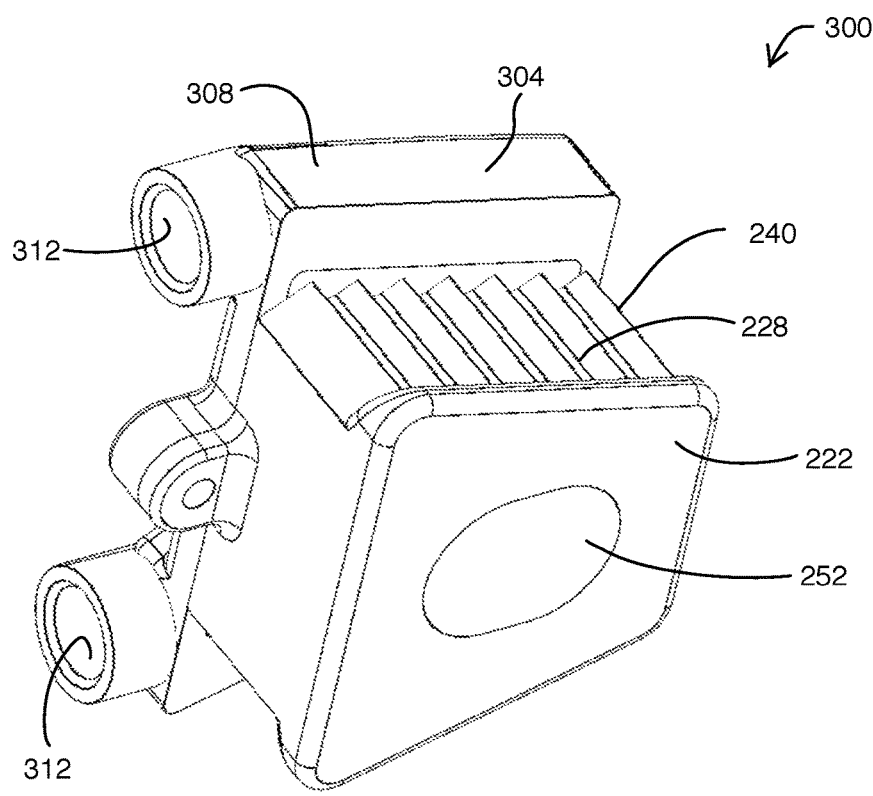
FIG. 18 is perspective view of another bite block including lights and a suction manifold.
Figure 19:
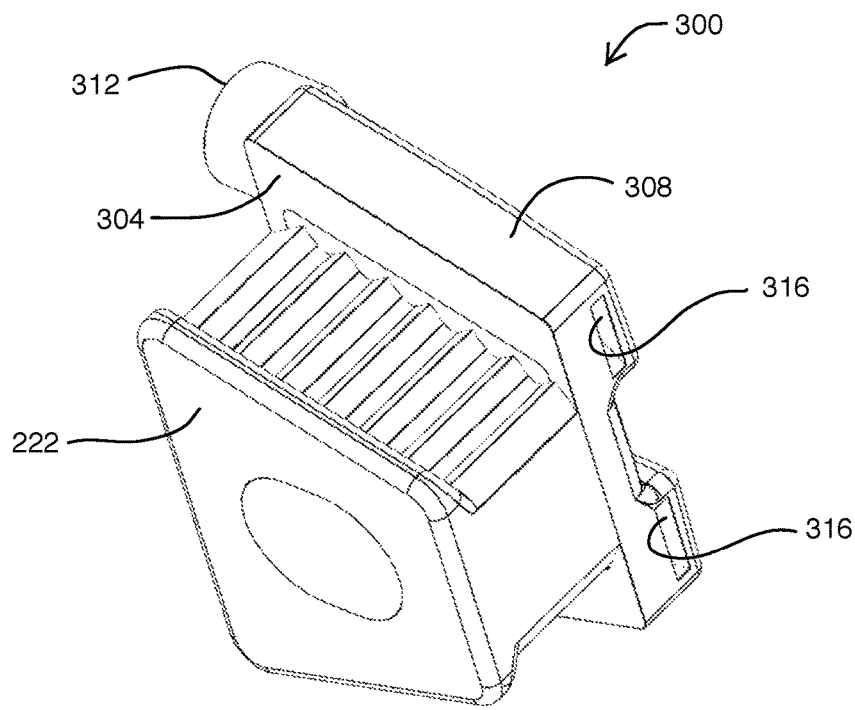
FIG. 19 is another perspective view of the bite block of FIG. 18.

FIGS. 16 and 17 better illustrate the space 208 of the bite block 200 of FIGS. 14 and 15. With reference to FIG. 16, a circuit board 268 supports the two LEDs 214 adjacent the window 252 of the first side wall 222. As illustrated, the LEDs 214 are positioned along the axis 236 in a horizontal orientation. The horizontal orientation better distributes light within the mouth during a procedure than does a vertical orientation. In addition, the use of two separate LEDs 214, and the positioning of those LEDs 214 near the second end of the bite block 200 (i.e., toward the back of the mouth) improves the lighting of the rear of the front teeth and the rear molars. In one construction, both LEDs 214 emit white light. However, in other constructions, one or both of the LEDs 214 is arranged to emit amber light (570-620 nm), blue light (405 nm plus or minus 25 nm), or blue-white light (430-580 nm). The LEDs 214 can then be controlled to provide unique colors or color mixing.

The power supply 212 is positioned behind the circuit board 268 as illustrated in FIG. 17. In preferred constructions, the power supply 212 is selected to provide sufficient power to the LEDs 214 for the necessary amount of time for a typical procedure (e.g., 1 hour). Since the bite block 200 of FIGS. 14-17 is intended to be a single-use device, the proper selection of the power supply 212 provides for a reduction in the cost of the bite block 200. In the illustrated construction, one or more batteries are used as the power supply 212. However, other power supplies 212, including an induction power supply could be employed. If an induction power supply is employed, it is preferably used in a device that can be re-used.

The switch 218 is also positioned behind the circuit board 268 and adjacent the second side wall 224. The switch 218 can be a simple switch that transitions between an on and off position, or between on, off, and other modes of operation. In another construction, a magnetic switch is provided that requires no direct physical contact but rather is actuated using a magnetic device, or key positioned adjacent the second side wall 224 outside the patient's mouth.

In use, the user (e.g., dentist, surgeon, etc.) first attaches dental floss or string to the floss retractor 248 and then places the bite block 200 into the patient's mouth. The first side wall 222 is positioned toward the interior of the mouth between the teeth and the tongue and the second side wall 224 is positioned between the teeth and the cheek. The larger size of the second side wall 224 reduces the likelihood that the bite block 200 will slip from the desired position. The LEDs 214 are actuated either prior to insertion into the patient's mouth or after. During the procedure, the user can cycle the LEDs 214 between their various modes by actuating the switch actuator 264. At the completion of the procedure, the bite block 200 is discarded.

The bite block 200 can be provided in a pre-sterilized package that includes one or multiple bite blocks 200. In addition, bite blocks 200 can be customized or configured for a particular procedure, thereby allowing the user to select the bite block 200 that provides the best quality and color of light for the particular procedure. Further, different size bite blocks 200 can be provided for use with patient's having different sized mouths. Thus, bite locks 200 suitable for use with children would be smaller than those used with adults.

Figure 20:
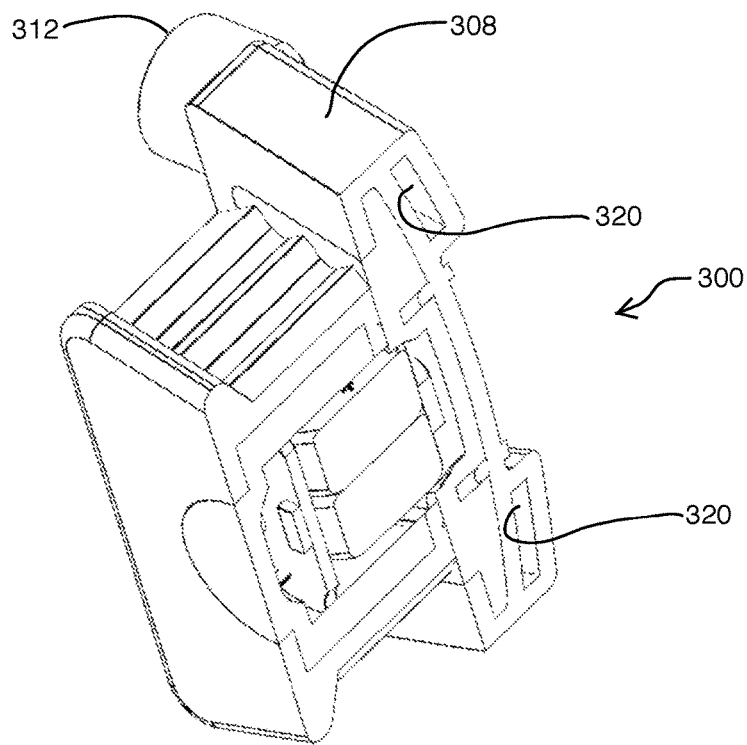
FIG. 20 is a perspective section view of the bite block of FIG. 18 illustrating the suction manifold.
Figure 21:
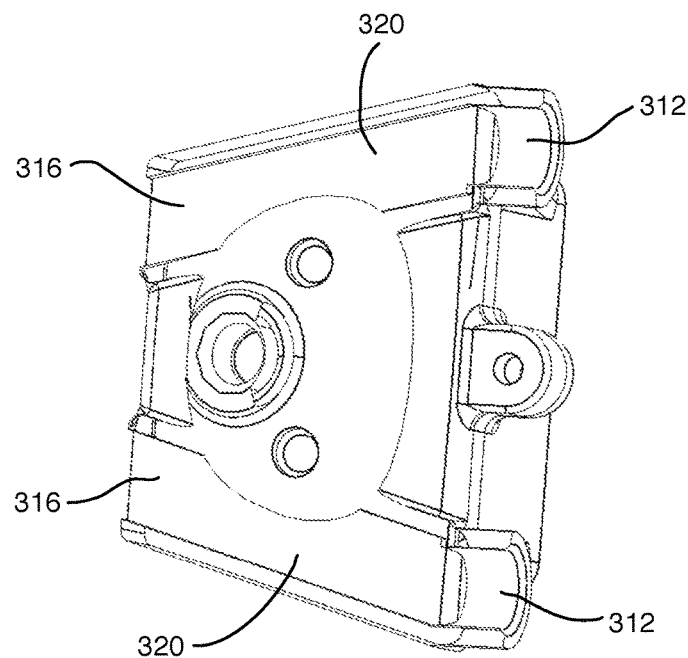
FIG. 21 is a perspective section view of the bite block of FIG. 18 illustrating the suction manifold.

FIGS. 18-21 illustrate another construction of a bite block 300 that is similar to the bite block 200 of FIGS. 14-17 but that further includes a second side wall 304 having a suction manifold 308. The suction manifold 308 includes two suction outlets 312 positioned at a first end of the bite block 300 which is positioned at the open end of the patient's mouth. The suction outlets 312 are sized and shaped to engage the standard suction devices commonly used by dentists and oral surgeons. Two suction inlets 316 are positioned at the opposite second end of the bite block 300 which is positioned near the patient's throat during a procedure. As illustrated in FIGS. 20 and 21, two flow paths 320 are formed as part of the suction manifold 308 with each flow path 320 extending between one of the inlets 316 and outlets 312. By separating the flow paths 320, the user can select only one of the flow paths 320 for use or could select both if desired. Of course, other arrangements of the flow paths 320, inlets 316, and outlets 312 are possible.

In the construction illustrated in FIGS. 18-21, the suction manifold 308 is formed as part of the second side wall 304 such that the two are inseparable components. However, in another construction, the bite block 200 of FIGS. 14-17 receives a separate piece that attaches to the second side wall 224 and operates as the suction manifold 308.

The bite block 300 of FIGS. 18-21 is used in the same manner as the bite block 200 of FIGS. 14-17. However, the suction manifold 308 allows the user to attach an external suction device to one or both of the suction outlets 312 to provide constant suction near the back of the patient's throat.

Figure 23:
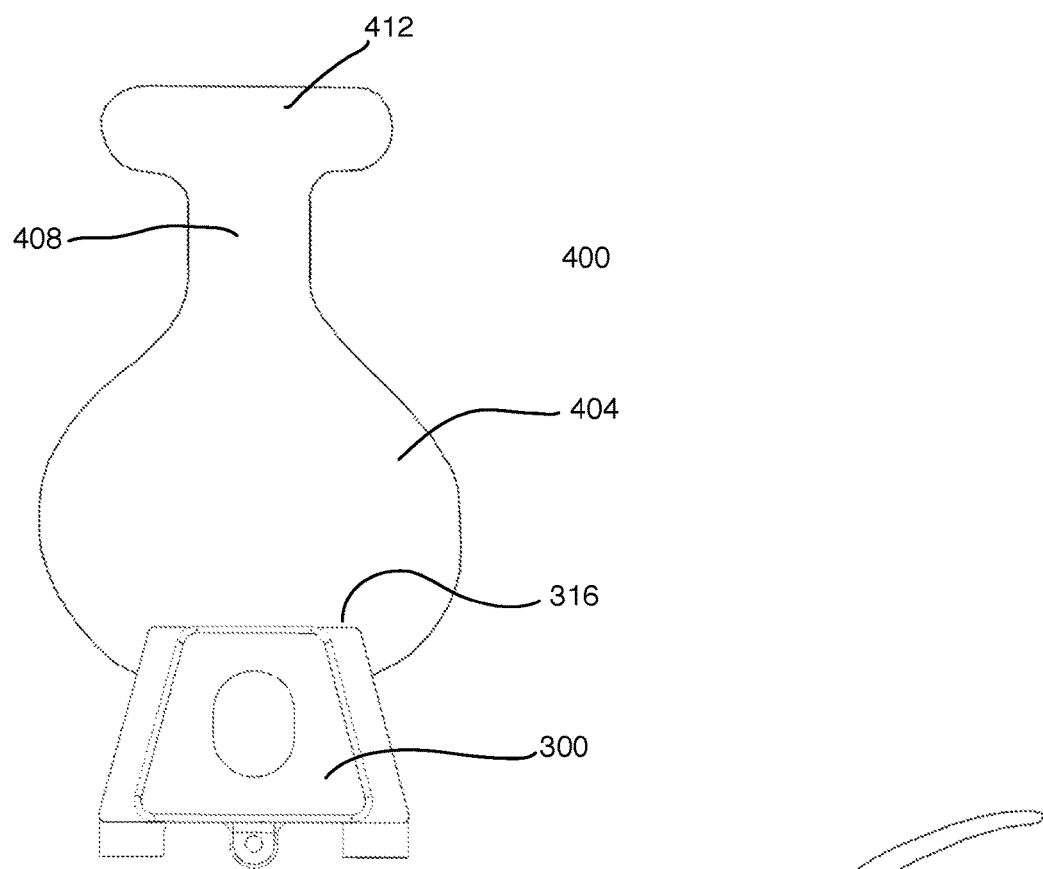
FIG. 23 is a side view of the bite block of FIG. 18 coupled to an isolation flap.
Figure 24:
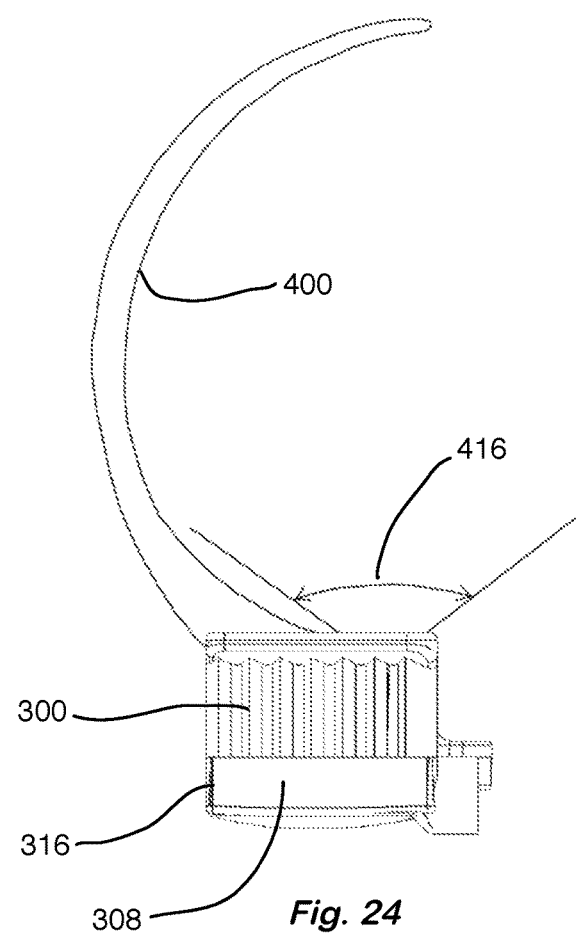
FIG. 24 is top view of the bite block and isolation flap of FIG. 23 shown in an in-use position.

FIGS. 23 and 24 illustrate the bite block 300 of FIGS. 18-21 with the addition of an isolation flap 400. In some constructions, the isolation flap 400 and the bite block 300 are formed as a single continuous component. However, in another construction the isolation flap 400 attaches to the bite block 300 for use only when needed. More specifically, the isolation flap 400 includes a male connector portion (not shown) that is received in one of the suction inlets 316 to attach the isolation flap 400 to the bite block 300.

The isolation flap 400 is formed from a resilient and flexible material to allow it to be manipulated into the desired position during use. The isolation flap 400 includes a large first portion 404 positioned adjacent the bite block 300, a second portion 408 positioned adjacent the first portion 404, and a third portion 412, that is preferably oval and positioned adjacent the second portion 408. Of course, other shapes and arrangements are possible.

FIG. 24 illustrates the isolation flap 400 in an in-use orientation. As illustrated, the isolation flap 400 extends from the rear (i.e., throat side) of the bite block 300 and is positioned such that the first portion 404 is disposed over the patient's throat. The narrow second portion 408 passes between the upper and lower teeth on the side of the mouth opposite the bite block 300, with the third portion 412 positioned between the teeth and the cheek to retain the isolation flap 400. In this position, the isolation flap 400 inhibits the entry of foreign objects into the patient's throat during the procedure. The suction manifold 308 allows for the continuous application of suction behind the isolation flap 400 to remove unwanted liquids.

With continued reference to FIG. 24, the isolation flap 400 is positioned and oriented to allow light to be emitted from the bite block 300 at a desired emission angle 416 to assure that the isolation flap 400 does not create any shadows or other unwanted effects in the mouth. In the illustrated construction, the emission angle 416 is about 120 degrees with other angles being possible.

Although the invention has been described in detail with reference to certain preferred embodiments, variations and modifications exist within the scope and spirit of one or more independent aspects of the invention as described.

What is claimed is:

1. A single use bite block comprising:
a body defining a first side wall, a second side wall, a first bite surface extending between the first side wall and the second side wall, and a second bite surface extending between the first side wall and the second side wall, the second side wall arranged to be positioned adjacent a patient's cheek;
a window formed as part of the first side wall;
an LED positioned within the body and positioned to emit light through the window;
a battery positioned within the body, the battery connected to the LED; and
a switch positioned within the body and actuatable through contact with the second side wall to selectively provide power to the LED, wherein the body defines an inseparable component that cannot be disassembled without destroying the body, and wherein the window is fixedly attached to the body
to define a watertight seal therebetween.

2. The bite block of claim 1, wherein the body and the window completely enclose the LED, the battery, and the switch and provide a water-proof barrier such that the bite block is a single use device.

3. The bite block of claim 1, wherein the first bite surface and the second bite surface are arranged at an acute angle with respect to one another, and wherein each of the first bite surface and the second bite surface includes a plurality of teeth each having a triangular cross section.

4. The bite block of claim 1, wherein the body portion is formed from a resilient opaque material and the window is formed from a translucent material.

5. The bite block of claim 1, further comprising a floss attachment portion arranged to receive a restraining floss.

6. The bite block of claim 1, wherein the LED is a first LED, the bite block further comprising a second LED, and wherein the first LED and the second LED are arranged along a line that is equidistant from the first bite surface and the second bite surface.

7. The bite block of claim 1, wherein the LED is arranged to emit light having a color of at least two of white light, amber light, blue light, and blue-white light.

8. The bite block of claim 7, wherein the switch is operable to cycle the LED between a first of the at least two colors of light, a second of the at least two colors of light, and an off condition.

9. The bite block of claim 1, wherein the second side wall is arranged to be disposed between the teeth and the cheek of a patient, and wherein the second side is larger than the first side.

10. The bite block of claim 1, further comprising an isolation flap coupled to the body and movable to a position in which a portion of the isolation flap covers a patient's throat.

11. A bite block comprising:
a first side wall defining a first surface arranged to be positioned between a patient's teeth and cheek;
a second side wall defining a second surface arranged to be positioned between a patient's teeth and tongue;
a first bite surface extending between the first side wall and the second side wall;
a second bite surface extending between the first side wall and the second side wall, the first bite surface arranged at an oblique angle with respect to the second bite surface and each of the first bite surface and the second bite surface being positioned equidistant from a central axis;
a first LED operable to emit white light, the first LED positioned on the central axis;
a second LED operable to emit light, the second LED positioned on the central axis and spaced apart from the first LED;
a window positioned to facilitate the transmission of light from each of the first LED and the second LED, the window formed to define a lens that focuses the light from at least one of the first LED and the second LED; and
a switch operable to selectively provide power to one of the first LED, the second LED or both the first LED and the second LED, the window, the first side wall, the second side wall, the first bite surface, and the second bite surface cooperating to fully enclose a space that contains the switch, the first LED, and the second LED.

12. The bite block of claim 11, wherein the second LED emits light having one of the following colors: amber light, blue light, and blue-white light.

13. The bite block of claim 11, wherein the first side wall, the second side wall, the first bite surface, and the second bite surface cooperate to substantially enclose a space and wherein the first LED and the second LED are disposed within the space adjacent the second side wall, and the switch is disposed within the space adjacent the first side wall.

14. The bite block of claim 13, further comprising a power supply disposed within the space and operable to deliver power to the first LED and the second LED.

15. The bite block of claim 14, wherein the power supply is a battery.

16. The bite block of claim 13, wherein the second side wall includes a window portion positioned to allow for the passage of light emitted by the first LED and the second LED.

17. The bite block of claim 11, further comprising a suction manifold coupled to the first side wall, the manifold including two inlets formed at one end, two outlets formed at an opposite end, and two flow spaces each extending between one of the inlets and outlets.

18. The bite block of claim 17, wherein the suction manifold is formed as one piece with the first side wall.

19. The bite block of claim 11, wherein the first LED has an emission angle that is less than 30 degrees.

20. The bite block of claim 19, wherein the first LED defines an emission axis and wherein the emission axis not normal to the second surface.

21. The bite block of claim 11, further comprising a first end wall and a second end wall, and wherein the first side wall, the second side wall, the first bite surface, the second bite surface, the first end wall and the second end wall are fixedly coupled to one another to enclose a water-tight space that cannot be opened without destroying the bite block.

\* \* \* \* \*